United States Patent [19]

Konno et al.

[11] 4,343,737
[45] Aug. 10, 1982

[54] PROCESS FOR PRODUCTION OF THIOLCARBAMATES AND THE THIOLCARBAMATES OBTAINED BY SAID PROCESS

[75] Inventors: Kazuhiko Konno; Atsushi Goh; Kunio Uchimura, all of Ami, Japan

[73] Assignee: Mitsubishi Petrochemical Co., Ltd., Japan

[21] Appl. No.: 247,502

[22] Filed: Mar. 25, 1981

[30] Foreign Application Priority Data

Mar. 31, 1980 [JP] Japan .................................. 55/40307

[51] Int. Cl.³ ................ C07D 211/60; C07D 207/24; C07D 209/32; C07C 155/02
[52] U.S. Cl. ............................ 260/239 BF; 546/245; 260/455 A; 260/326.4; 568/67; 568/64; 568/65; 568/62
[58] Field of Search .......... 260/455 A, 326.4, 239 BF; 546/245; 568/67, 64, 65, 62

[56] References Cited

U.S. PATENT DOCUMENTS 2,642,450  6/1953  Weijlard et al. ................. 260/455 A
3,282,978  11/1966  Swakon ........................... 260/455 A
4,147,715  4/1979  Tilles et al. ....................... 546/245

OTHER PUBLICATIONS

Reid, Organic Chemistry of Bivalent Sulfur, vol. I, Chemical Publishing Co., Inc., 212 Fifth Avenue, N.Y., p. 19.

*Primary Examiner*—Henry R. Jiles
*Assistant Examiner*—Robert C. Whittenbaugh
*Attorney, Agent, or Firm*—Wenderoth, Lind & Ponack

[57] ABSTRACT

A process for producing a thiolcarbamate compound of the following formula

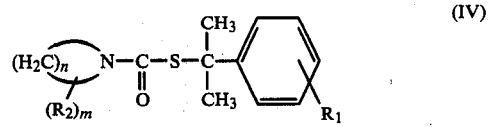

wherein $R_1$ represents a hydrogen atom, an alkyl group having 1 to 5 carbon atoms, an alkoxy group having 1 to 5 carbon atoms, a halogen atom or a nitro group, $R_2$ represents a hydrogen atom or an alkyl group having 1 to 4 carbon atoms, m is 1 or 2, and n is an integer of 4 to 6, which comprises reacting an α-methylstyrene of the following formula

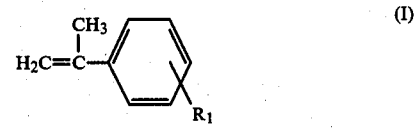

wherein $R_1$ is as defined above,
or its dimer with hydrogen sulfide in the presence of a catalyst to form a mercaptan of the following formula

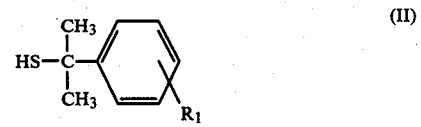

wherein $R_1$ is as defined above, and reacting the mercaptan of formula (II) with a carbamoyl chloride of the following formula

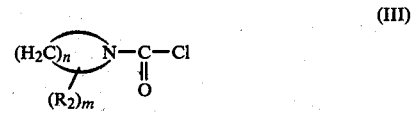

wherein $R_2$, m and n are as defined.

16 Claims, No Drawings

PROCESS FOR PRODUCTION OF THIOLCARBAMATES AND THE THIOLCARBAMATES OBTAINED BY SAID PROCESS

This invention relates to a new process for producing known thiolcarbamate derivatives of the following formula

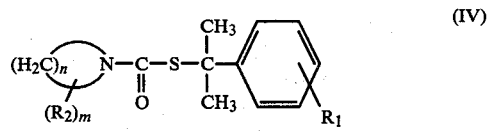
(IV)

wherein $R_1$ represents a hydrogen atom, a halogen atom, an alkyl group having 1 to 5 carbon atoms, an alkoxy group having 1 to 5 carbon atoms, or a nitro group, $R_2$ represents a hydrogen atom or an alkyl group having 1 to 4 carbon atoms, m is 1 or 2, and n is an integer of 4 to 6,
which have herbicidal activity (for example, disclosed in Japanese Laid-Open Patent Publication No. 98331/1976). According to this process, the thiolcarbamates of formula (IV) can be produced in high purity and yield with industrial advantage.

The above-cited Japanese patent document discloses the following process for producing the compound of formula (IV).

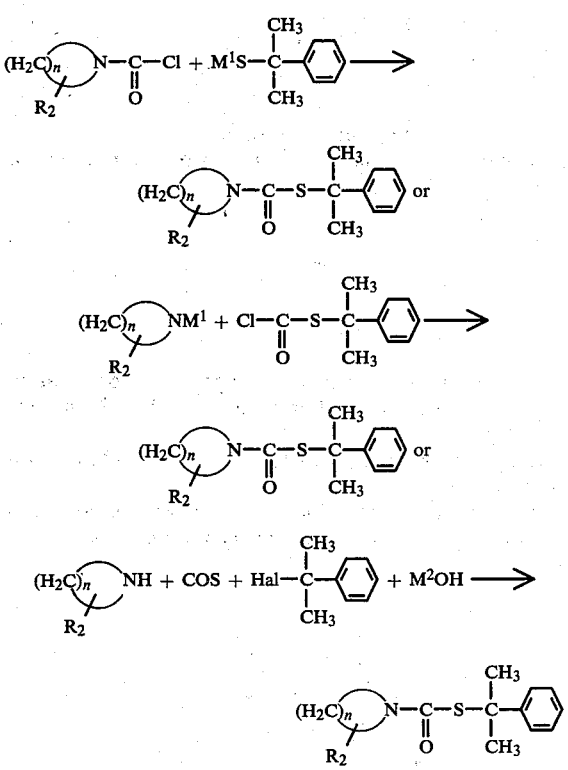

In the above formulae, n and $R_2$ are as defined above with regard to formula (IV), $M^1$ represents a hydrogen atom or an alkali metal atom, and $M^2$ represents an alkali metal or an ammonium group.

This patent document, however, fails to mention a process for producing

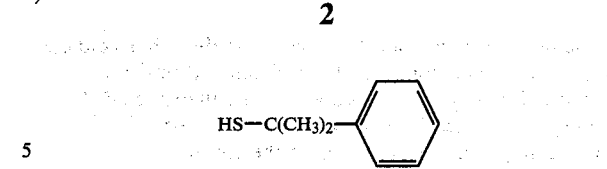

which is embraced with the formula

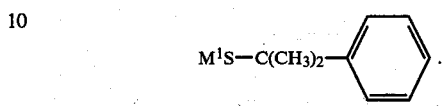

Some methods for synthesizing such benzylmercaptans have been suggested heretofore, but none of them have proved to be industrially satisfactory.

For example, it is known to produce benzylmercaptans by the vapor-phase catalytic reaction of benzyl alcohols with hydrogen sulfide (Bull. Soc. Chim., p. 322, 1977). This method has the disadvantage that the yield of the product is relatively low except the synthesis of a primary mercaptan from a primary alcohol. In particular, when this method is applied to the reaction of a tertiary alcohol, conversion of it to an olefin by dehydration reaction takes place vigorously, and the corresponding mercaptan cannot be obtained in satisfactory yields and with satisfactory selectivity.

A method for synthesizing benzylmercaptans by reacting benzyl halides with an aqueous solution of an alkali hydrosulfide is also known [Ann. Chim., II, 1, 359, 1934]. According to this method, benzylmercaptans can be synthesized in fairly high yields from primary and secondary benzyl halides. When, however, tertiary benzyl halides are used, formation of olefins by dehydrohalogenation or formation of alcohols by hydrolysis become conspicuous, and the yields of the benzylmercaptans are considerably low.

Another suggested method for producing benzylmercaptans starts from benzyl halides and goes through isothiuronium salts (Bull. Soc. Chim., 1961, page 2225). This method, however, has the same defect as the aforesaid method involving use of an aqueous solution of an alkali metal hydrosulfide.

It is also known to synthesize benzylmercaptans by reacting 2-nitro-2-phenylpropanes with sodium sulfide and sulfur (J. Am. Chem. Soc., 100, p. 7086, 1978). This method gives tertiary benzylmercaptans in high yields, but is not suitable for industrial production because the synthesis and procurement of the starting 2-nitro-2-phenylpropanes are difficult.

Thus, the conventional processes for producing secondary or tertiary benzylmercaptans have many difficulties, and it has been difficult to obtain in high yields with industrial advantage benzylmercaptans of the formula

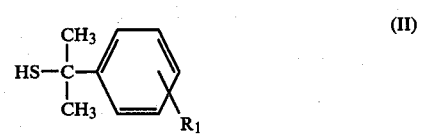
(II)

wherein $R_1$ is as defined with regard to formula (IV), which are used in the synthesis of the compounds of formula (IV).

The present inventors made investigations in order to develop a new synthetic process which can afford thiolcarbamates of formula (IV) having excellent herbicidal activity advantageously in high yields and purities.

These investigations have led to the unexpected discovery that by catalytically contacting aromatic olefins, particularly α-methylstyrenes of the formula

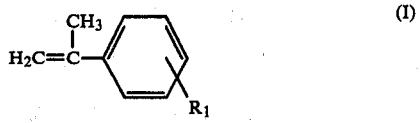

wherein $R_1$ is as defined above with regard to formula (IV), or their dimers with hydrogen sulfide in the presence of an addition-reaction catalyst, ionic addition-reaction between them takes place selectively with industrial advantage to give benzylmercaptans of formula (II) in high yields and purities.

Based on the above discovery that the α-methylstyrene of formula (I) which readily polymerizes by itself and hydrogen sulfide selectively form the compound of formula (II) by addition reaction in the presence of a catalyst, thus giving the compound of formula (II) in high yields, the present inventors have found that the thiolcarbamate derivatives of formula (IV) can be produced from the compounds of formula (I) with industrial advantage in high yields.

It is an object of this invention therefore to provide a new process for producing industrially producing the compounds of formula (IV) having herbicidal activity.

The above and other objects and advantages of this invention will become more apparent from the following description.

According to the process of this invention, the thiolcarbamate derivatives of formula (IV) can be produced in high yields with industrial advantage by a process which comprises (1) reacting an α-methylstyrene of the formula

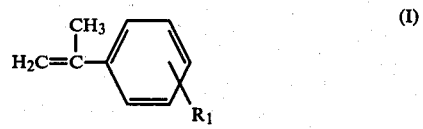

wherein $R_1$ represents a hydrogen atom, an alkyl group having 1 to 5 carbon atoms, an alkoxy group having 1 to 5 carbon atoms, a halogen atom or a nitro group, or a dimer thereof with hydrogen sulfide in the presence of a catalyst to give a mercaptan of the formula

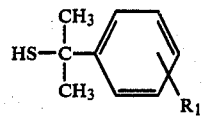

wherein $R_1$ is as defined above, and (2) reacting the mercaptan with a carbamoyl chloride of the formula

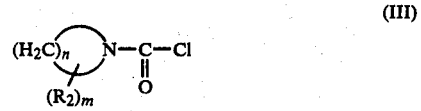

wherein $R_2$ represents a hydrogen atom or an alkyl group having 1 to 4 carbon atoms, m is 1 or 2, and n is an integer of 4 to 6.

This process is referred to herein as the carbamoyl chloride process.

According to the process of this invention, the thiolcarbamate derivatives of formula (IV) can also be produced in high yields with industrial advantage by a process which comprises reacting a mercaptan of formula (II) obtained in the same way as in the above process with phosgene to form a chlorothioformate of the formula

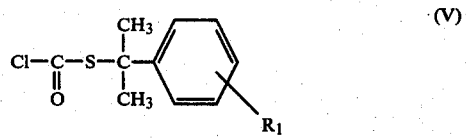

wherein $R_1$ is as defined above, and then reacting the resulting chlorothioformate with an imine of the formula

wherein $R_2$ represents a hydrogen atom or an alkyl group having 1 to 4 carbon atoms, m is 1 or 2, and n is an integer of 4 to 6.

This process is referred to herein as the chlorothioformate process.

The carbamoyl chloride process and the chlorothioformate process are schematically shown as follows:

(A) Carbamoyl chloride process

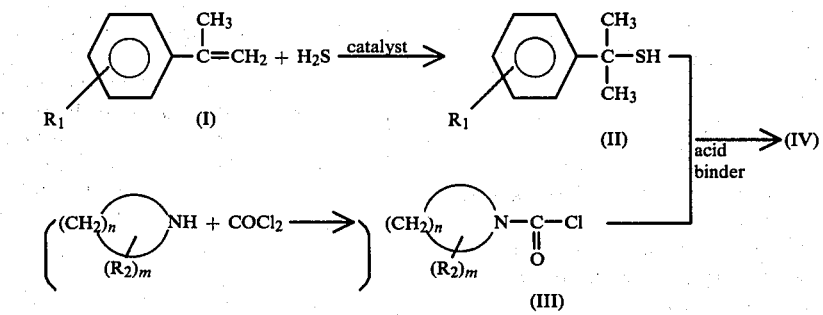

(B) Chlorothioformate process

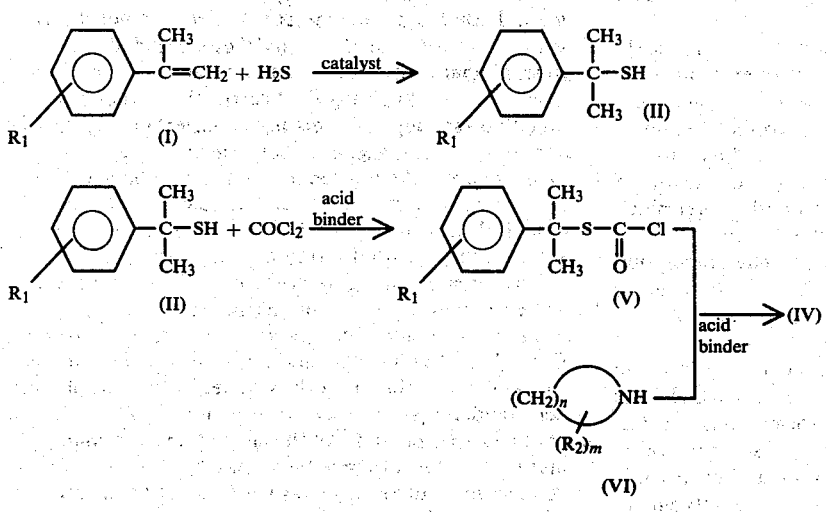

In formulae (I), (II), (IV) and (V), examples of the alkyl group having 1 to 5 carbon atoms for $R_1$ are methyl, ethyl, n-propyl, i-propyl, n-butyl, i-butyl, sec-butyl, tert-butyl, n-amyl, i-amyl, sec-amyl and tert-amyl. Examples of the alkoxy groups having 1 to 5 carbon atoms include methoxy, ethoxy, n-propoxy, i-propoxy, n-butoxy, i-butoxy, sec-butoxy, tert-butoxy, n-amyloxy and sec-amyloxy. Examples of the halogen atom are fluorine, chlorine, bromine and iodine. Examples of the alkyl group having 1 to 4 carbon atoms for $R_2$ in formulae (III), (IV) and (VI) are methyl, ethyl, n-propyl, i-propyl, n-butyl, i-butyl, sec-butyl and tert-butyl.

In the practice of the process of this invention, the dimethylbenzylmercaptans of formula (II) can be formed by catalytically reacting the α-methylstyrene of formula (I) or its dimer with hydrogen sulfide in the presence of an addition-reaction catalyst in the presence or absence of a nonpolar organic solvent. The reaction can be performed either in the liquid phase (in a homogeneous or heterogeneous system) and the vapor phase. The liquid-phase catalytic reaction, however, is preferred.

Examples of the addition-reaction catalyst used in the catalytic addition reaction between the α-methylstyrene of formula (I) or its dimer and hydrogen sulfide include phosphorus; phosphorus-containing compounds such as phosphoric acids and the anhydrides thereof (e.g., meta-phosphoric acid, pyrophosphoric acid, ortho-phosphoric acid, triphosphoric acid, tetraphosphoric acid, and diphosphorus pentoxide and the anhydrides thereof), phosphorus oxides (e.g., phosphorus suboxide, diphosphorus trioxide and diphosphorus tetroxide), and phosphorus sulfides (e.g., tetraphosphorus trisulfide, tetraphosphorus pentasulfide, tetraphosphorus heptasulfide and diphosphorus pentasulfide); sulfuric acid and sulfonic acids such as sulfonic acid, benzenesulfonic acid and p-toluenesulfonic acid; trifluoroacetic acid; acid clays; active clays; and oxides or sulfides of metals, preferably metals of Groups IV to VIII of the periodic table, such as tungsten oxide, tungsten sulfide, dititanium trioxide, titanium dioxide, titanium monosulfide, titanium sesquisulfide, iron oxide, iron sulfide, vanadium oxide, vanadium sulfide, vanadium sesquisulfide, vanadium pentasulfide and vanadium tetrasulfide. Of these, the phosphorus-containing compounds, especially phosphorus sulfides and phosphoric acids and the anhydrides of these, and active clays are preferred.

These addition-reaction catalyst may be used singly or in combination with each other. Furthermore, these catalysts can be used supported on suitable carriers. Examples of such carriers are activated carbon, silica gel, alumina gel, asbestos, pumice, diatomaceous earth, glass and potter's earth.

The reaction may be carried out in the liquid phase (in a homogeneous system or in a heterogeneous system) and in the vapor phase.

For example, the liquid phase catalytic reaction may be carried out by passing the α-methylstyrene of formula (I) or its dimer which is liquid under the reaction conditions and hydrogen sulfide gas concurrently or countercurrently in the presence or absence of an inert organic solvent through a reaction zone having a catalyst layer.

Or the liquid phase catalytic reaction may also be performed by introducing hydrogen sulfide gas into a liquid phase system containing the α-methylstyrene of formula (I) or its dimer and the catalyst in the presence or absence of an inert organic solvent thereby to effect contacting between the reaction materials.

In performing the reaction for forming the mercaptan of formula (II), the amount of the catalyst can be properly selected. For example, it is about 0.01 to about 200 mole% based on the α-methylstyrene of formula (I) or its dimer preferably about 1 to about 100 mole%, more preferably about 5 to about 15 mole%.

In performing the reaction in the liquid phase, the starting α-methylstyrene of formula (I) or its dimer may be used without dilution. Dilution of the starting compound with a suitable inert organic solvent and the performance of the reaction in the presence or absence of a polymerization inhibitor are preferred in order to inhibit side-reactions such as polymerization and obtain the mercaptan in high purities and high yields. The amount of the inert organic solvent may be selected properly from the standpoint of the volume efficiency of the reaction zone and the increase of the yield. Preferably, it is used such that the concentration of the α-methylstyrene of formula (I) or its dimer in the solvent is about 1 to about 100% by weight, preferably about 20 to about 60% by weight, especially preferably about 25 to about 50% by weight.

The amount of hydrogen sulfide can be properly selected depending upon the mode of operation of the liquid phase catalytic reaction, the reaction conditions, etc. It may be roughly stoichiometric to the amount of the α-methylstyrene of formula (I) or its dimer. If desired, it may be used in an excessive amount. The rate of feeding hydrogen sulfide can be properly determined depending upon the mode of practising the liquid-phase catalytic reaction, etc. For example, it may correspond to the rate of consumption of it in the reaction zone or is slightly higher than it. If desired, faster rates of feeding may be employed.

The solvent which may be used in the liquid phase catalytic reaction is an inert organic solvent which does not react with the compounds of formula (I) and (II) and the catalyst. Such an inert organic solvent can be properly selected, but the use of non-polar inert organic solvents is preferred. Examples of such a solvent include aliphatic saturated hydrocarbons such as pentane, hexane, heptane, octane, nonane and decane; alicyclic hydrocarbons such as cyclopentane, cyclohexane, cycloheptane and cyclooctane; aromatic hydrocarbons such as benzene, toluene, ethylbenzene, n-propylbenzene, i-propylbenzene and xylene; halogenated hydrocarbons such as dichloromethane, chloroform, carbon tetrachloride and 1,1-dichloroethane; fatty acid esters such as methyl formate, ethyl formate, propyl formate, butyl formate, methyl acetate, ethyl acetate, propyl acetate, butyl acetate, methyl propionate, ethyl propionate and propyl propionate; and ethers such as diethyl ether, di-n-propyl ether, di-i-propyl ether, tetrahydrofuran, tetrahydropyran, 1,4-dioxane, ethylene glycol dimethyl ether and ethylene glycol diethyl ether. They may be used as mixtures with each other.

The reaction temperature may also be selected properly. For example, it is from room temperature to about 180° C., preferably from about 25° C. to about 175° C., especially preferably from about 40° C. to about 120° C. The reaction time can be selected properly depending upon the reaction temperature, the type of the starting compound of formula (II), the type and amount of the catalyst, the rate of feeding hydrogen sulfide, the mode of practice of the liquid-phase catalytic reaction, etc. For example, it is about 0.5 hour to about 10 hours.

According to the process of this invention, the desired thiolcarbamate compound of formula (IV) can be produced advantageously from the resulting dimethylbenzylmercaptan of formula (II) by using (A) the carbamoyl chloride process or (B) the chlorothioformate process.

According to the process (A), the desired compound of formula (IV) can be obtained by reacting the mercaptan (II) with the carbamoyl chloride (III) preferably in the presence of an acid binder in an inert organic solvent.

Examples of the acid binder that can be used include alkali metal bicarbonates and carbonates such as sodium bicarbonate, sodium carbonate and potassium carbonate, and organic bases such as triethylamine, pyridine and picoline. The reaction may be performed in the presence of the added acid binder. Or the reaction can be performed by forming an alkali metal salt of the mercaptan of formula (II) in advance.

Examples of the inert organic solvent are ethers such as diethyl ether, di-n-propyl ether, di-i-propyl ether, tetrahydrofuran, tetrahydropyran, ethylene glycol dimethyl ether and ethylene glycol diethyl ether; ketones such as acetone, methyl ethyl ketone and diethyl ketone; aliphatic nitriles such as acetonitrile and propionitrile; aliphatic or aromatic hydrocarbons such as pentane, hexane, heptane, octane, cyclopentane, cyclohexane, benzene, toluene, ethylbenzene and xylene; halogenated hydrocarbons such as dichloromethane, chloroform, carbon tetrachloride and 1,1-dichloroethane; and dimethyl formamide; and dimethyl sulfoxide. These solvents may be used singly or in combination.

The reaction can be performed at room temperature, and cooling or heating is not particularly necessary. For example, the reaction temperature may be from about 0° C. to about 120° C. The amounts of the acid binder and the solvent can be properly selected. For example, the acid binder may be used in an amount of about 1 to about 3 moles per mole of the mercaptan of formula (II), and the amount of the solvent may be about 2 to about 20 parts by volume per part by volume of the mercaptan of formula (II).

The carbamoyl chloride of formula (III) used in the above reaction can be easily obtained by a known reaction from an imine of the formula

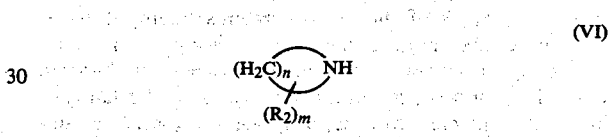

(VI)

wherein $R_2$ represents a hydrogen atom or an alkyl group having 1 to 4 carbon atoms, m is 1 or 2, and n is an integer of 4 to 6, and phosgene $COCl_2$. For example, as shown in Chem. Listy., 46, 762–765 (1952), the reaction of the imine with an excess of phosgene in an inert solvent under reflux readily gives the carbamoyl chloride of formula (III) in good yields.

According to the chlorothioformate process (B), the desired product of formula (IV) can be obtained by reacting the mercaptan of formula (II) obtained as above with phosgene to form a chlorothioformate of the formula

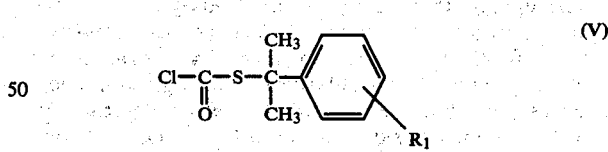

(V)

wherein $R_1$ is as defined,
and reacting the compound (V) with the imine of formula (VI).

In this embodiment, phosgene dimer may be used as the phosgene to be reacted with the mercaptan (II).

The reaction can be performed, for example, in an inert organic solvent, preferably in the presence of an acid binder.

The same acid binders as exemplified with regard to the process (A) may be used in the process (B). Furthermore, as stated with regard to the process (A), the reaction may be carried out in the presence of the added acid binder. Or the reaction may be carried out after an alkali metal salt of the mercaptan (II) is formed in advance. Examples of the inert organic solvent are the same as these given hereinabove with regard to the reaction of the mercaptan (II) with the carbamoyl chloride (III) in the process (A). The reaction temperature is, for example, from −20° C. to 100° C., and the reaction time is, for example, from 1 to 10 hours. The mole ratio of the reactants can be suitably selected. For example, about 1 to about 10 moles of phosgene may be used per mole of the mercaptan of formula (II).

The reaction of the chlorothioformate of formula (V) so formed with the imine of formula (VI) may be carried out preferably in the presence of an acid binder, in an inert organic solvent, in the same way as stated hereinabove with regard to the reaction of the mercaptan (II) with the carbamoyl chloride (III) in the process (A). The reaction temperature is, for example, from 0° C. to 100° C., and the reaction time is, for example, from 1 to 10 hours. The mole ratio of the reactants can be suitably selected. For example, about 1 to about 1.5 moles of the imine of formula (VI) may be used per mole of the compound of formula (V).

Thus, according to the process of this invention, the thiolcarbamate compound of formula (IV) can be produced in high yields with industrial advantage from the α-methylstyrene of formula (I) or its dimer.

Typical examples of the compounds of general formula (IV) are listed below.

(1) N-(α,α-dimethylbenzylthio-carbonyl)piperidine,
(2) N-(α,α-dimethylbenzylthio-carbonyl)pyrrolidine,
(3) N-(α,α-dimethylbenzylthio-carbonyl)hexamethyleneimine,
(4) N-(α,α-dimethylbenzylthio-carbonyl)-2-methylpiperidine,
(5) N-(α,α-dimethylbenzylthio-carbonyl)-3-methylpiperidine,
(6) N-(α,α-dimethylbenzylthio-carbonyl)-4-methylpiperidine,
(7) N-(α,α-dimethylbenzylthio-carbonyl)-2,4-dimethylpiperidine,
(8) N-(α,α-4-trimethylbenzylthio-carbonyl)hexamethyleneimine,
(9) N-(α,α-dimethyl-4-methoxybenzylthio-carbonyl)-hexamethyleneimine,
(10) N-(α,α-dimethyl-4-chlorobenzylthio-carbonyl)hexamethyleneimine, and
(11) N-(α,α-dimethyl-4-nitrobenzylthio-carbonyl)hexamethyleneimine.

The following Examples illustrate the present invention more specifically without any intention of limiting the invention thereby.

EXAMPLE 1

Synthesis of α,α-dimethylbenzylmercaptan

A 300 ml three-necked flat-bottomed flask equipped with a gas blowing tube, a mercury thermometer and a Teflon stirrer therein was charged with 35.4 g (0.3 mole) of α-methylstyrene, 106 ml of dioxane and 9 g (0.04 mole) of phosphorus pentasulfide as a catalyst. The inside of the reaction system was purged with hydrogen sulfide, and the flow rate of hydrogen sulfide was adjusted to 150 cc/min. Then, the reactor was put into an oil bath controlled to 60° C., and stirring of the reaction system and bubbling of hydrogen sulfide were started. When the temperature of the reaction mixture reached 60° C., the reaction was performed for 4 hours. Then, the supply of hydrogen sulfide was stopped, and while bubbling nitrogen through the reaction system, the reaction mixture was cooled to room temperature. The reaction mixture was suction-filtered to remove phosphorus pentasulfide, and the filtrate was analyzed by a gas-chromatographic internal standard method. The analysis showed the product to contain 1.4 g of unreacted α-methylstyrene and 40.3 g of α,α-dimethylbenzyl mercaptan. (The conversion 96%; selectivity 92 mole%; yield 88 mole%.)

To the reaction mixture (filtrate) was added 200 ml of a 4% aqueous solution of sodium hydroxide, and the mercaptan was extracted into the aqueous layer. The aqueous layer was then acidified with hydrochloric acid and then extracted with 100 ml of n-hexane three times. The n-hexane extracts were dried, concentrated and distilled under reduced pressure to give 38.5 g of α,α-dimethylbenzylmercaptan (b.p. 57°–65° C./1 mm). (Yield 81%; purity determined by gas chromatography 96%).

EXAMPLE 2

Synthesis of N-(α,α-dimethylbenzylthiocarbonyl)piperidine (by the carbamoyl chloride process)

6.08 g (0.04 mole) of α,α-dimethylbenzylmercaptan was dissolved in 50 ml of toluene, and 4.0 g (0.04 mole) of a 40% aqueous solution of sodium hydroxide was added dropwise at room temperature. The resulting solution was heated under refluxing of toluene to separate water azeotropically. Subsequent removal of toluene gave 6.96 g of a white solid. 50 ml of the white solid was dissolved in tetrahydrofuran, and 5.9 g (0.04 mole) of piperidine-1-carbonyl chloride was added dropwise over about 30 minutes with stirring under ice cooling. After the addition, the mixture was stirred at room temperature for about 1 hour, and then tetrahydrofuran was distilled off. The residue was dissolved in cyclohexane, washed with water, and dried over anhydrous sodium sulfate, followed by distilling off the cyclohexane. The residue was purified by column chromatography (silica gel as an adsorbent; and benzenedichloromethane as an eluent) to give 9.0 g of the desired product (yield 85.2%).

EXAMPLE 3

Synthesis of α,α-dimethylbenzylthio-carbonyl chloride 178 g (0.90 mole) of phosgene dimer was dissolved in 200 ml of hexane, and with stirring under ice cooling, a mixture of 45.6 g (0.30 mole) of α,α-dimethylbenzylmercaptan, 33.3 g (0.33 mole) of triethylamine and 100 ml of hexane was added dropwise over the course of about 30 minutes. The mixture was then stirred at room temperature for 1 hour. The resulting triethylamine hydrochloride was separated by filtration. When the excess of phosgene dimer and hexane were distilled off from the filtrate, 55.0 g of the desired product was obtained as a pale yellow oil (yield 85.5%).

EXAMPLE 4

Synthesis of N-(α,α-dimethylbenzylthio-carbonyl)piperidine (by the chlorothioformate process)

3.4 g (0.04 mole) of piperidine and 4.04 g (0.04 mole) of triethylamine were dissolved in 75 ml of dichloromethane, and with stirring under ice cooling, 8.58 g (0.04 mole) of α,α-dimethylbenzylthio-carbonyl chloride was added dropwise over the course of about 30 minutes. After the addition, the mixture was stirred at room temperature for about 1 hour. The reaction mixture was washed with water and dried over anhydrous sodium sulfate, followed by distilling off dichloromethane. The residue was purified by column chromatography (silica gel as an adsorbent and benzene-dichloromethane as an eluent) to give 8.7 g of the desired product (yield 82.4%).

What we claim is:

1. A process for producing a thiolcarbamate compound of the following formula

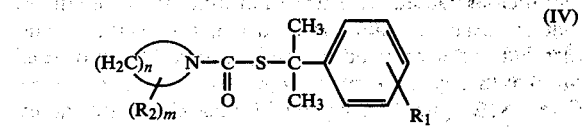

wherein $R_1$ represents a hydrogen atom, an alkyl group having 1 to 5 carbon atoms, an alkoxy group having 1 to 5 carbon atoms, a halogen atom or a nitro group, $R_2$ represents a hydrogen atom or an alkyl group having 1 to 4 carbon atoms, m is 1 or 2, and n is an integer of 4 to 6, which comprises reacting an α-methylstyrene of the following formula

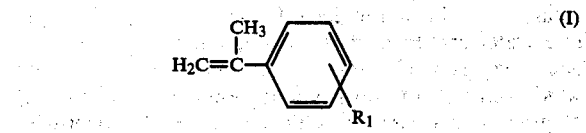

wherein $R_1$ is as defined above,
or its dimer with hydrogen sulfide in the presence of $P_2S_5$ or $P_4S_7$ as a catalyst to form a mercaptan of the following formula

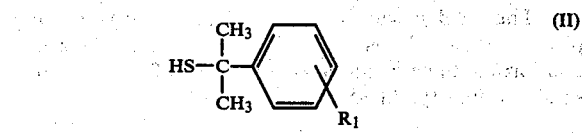

wherein $R_1$ is as defined above,
and reacting the mercaptan of formula (II) with a carbamoyl chloride of the following formula

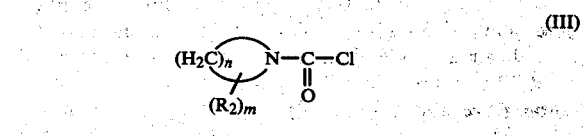

wherein $R_2$, m and n are as defined.

2. The process of claim 1 wherein the reaction of the α-methylstyrene of formula (I) or its dimer with hydrogen sulfide is carried out at room temperature to about 180° C.

3. The process of claim 1 wherein the reaction of the α-methylstyrene of formula (I) or its dimer with hydrogen sulfide is carried out in an inert organic solvent.

4. The process of claim 1 wherein the reaction of the mercaptan of formula (II) with the carbamoyl chloride of formula (III) is carried out at about 0° C. to about 120° C.

5. The process of claim 1 wherein the reaction of the mercaptan of formula (II) with the carbamoyl chloride of formula (III) is carried out in the presence of an acid binder.

6. The process of claim 1 wherein the reaction of the mercaptan of formula (II) with the carbamoyl chloride of formula (III) is carried out in an inert organic solvent.

7. A process for producing a thiolcarbamate compound of the following formula

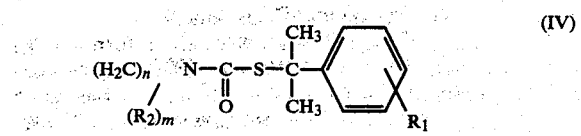

wherein $R_1$ represents a hydrogen atom, an alkyl group having 1 to 5 carbon atoms, an alkoxy group having 1 to 5 carbon atoms, a halogen atom or a nitro group, $R_2$ represents a hydrogen atom or an alkyl group having 1 to 4 carbon atoms, m is 1 or 2, and n is an integer of 4 to 6, which comprises reacting an α-methylstyrene of the following formula

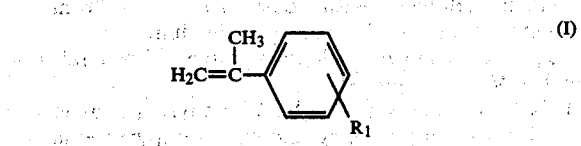

wherein $R_1$ is as defined above,
or its dimer with hydrogen sulfide in the presence of $P_2S_5$ or $P_4S_7$ as a catalyst to form a mercaptan of the following formula

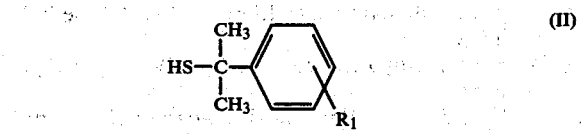

wherein $R_1$ is as defined above,
reacting a mercaptan of formula (II) with phosgene to form a chlorothioformate of the following formula

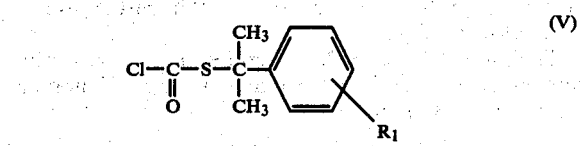

wherein $R_1$ is as defined above,
and reacting the compound of formula (V) with an imine of the following formula

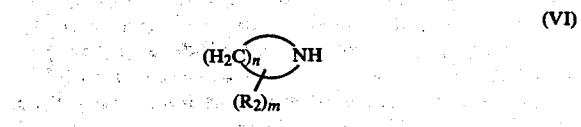

wherein $R_2$, m and n are as defined above.

8. The process of claim 7 wherein the reaction of the α-methylstyrene of formula (I) or its dimer with hydrogen sulfide is carried out at room temperature to about 180° C.

9. The process of claim 7 wherein the reaction of the α-methylstyrene of formula (I) or its dimer with hydrogen sulfide is carried out in an inert organic solvent.

10. The process of claim 7 wherein the reaction of the mercaptan of formula (II) with phosgene is carried out at about −20° to about 100° C.

11. The process of claim 7 wherein the reaction of the mercaptan of formula (II) with phosgene is carried out in the presence of an acid binder.

12. The process of claim 7 wherein the reaction of the mercaptan of formula (II) with phosgene is carried out in an inert organic solvent.

13. The process of claim 7 wherein the reaction of the chlorothioformate of formula (V) with the imine of formula (VI) is carried out at about 0° to about 100° C.

14. The process of claim 7 wherein the reaction of the compound of formula (V) with the imine of formula (VI) is carried out in the presence of an acid binder.

15. The process of claim 7 wherein the reaction of the compound of formula (V) with the imine of formula (VI) is carried out in an inert organic solvent.

16. A process for producing a mercaptan of the formula

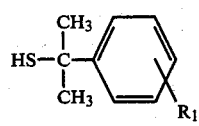

(II)

wherein $R_1$ represents a hydrogen atom, an alkyl group having 1 to 5 carbon atoms, an alkoxy group having 1 to 5 carbon atoms, a halogen atom or a nitro group, $R_2$ represents a hydrogen atom or an alkyl group having 1 to 4 carbon atoms, m is 1 or 2, and n is an integer of 4 to 6, which comprises reacting an α-methylstyrene of the following formula

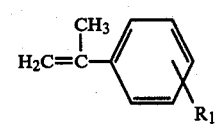

(I)

wherein $R_1$ is as defined above,
or its dimer with hydrogen sulfide in the presence of $P_2S_5$ or $P_4S_7$ as a catalyst.

* * * * *

UNITED STATES PATENT AND TRADEMARK OFFICE
CERTIFICATE OF CORRECTION

PATENT NO. : 4,343,737
DATED : August 10, 1982
INVENTOR(S) : Kazuhiko KONNO, Atsushi GOH, and Kunio UCHIMURA It is certified that error appears in the above—identified patent and that said Letters Patent is hereby corrected as shown below:

Claim 7, formula (IV), rewrite as follows:

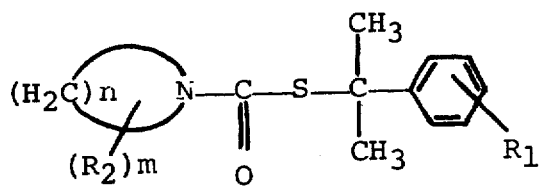

Signed and Sealed this

First Day of March 1983

[SEAL]

Attest:

GERALD J. MOSSINGHOFF

Attesting Officer      Commissioner of Patents and Trademarks